United States Patent [19]

Kubota

[11] 4,134,930
[45] Jan. 16, 1979

[54] RESINOUS MATERIALS FOR RESTORING CROWNS

[75] Inventor: Takao Kubota, Sayama, Japan

[73] Assignee: G-C Dental Industrial Corp., Tokyo, Japan

[21] Appl. No.: 750,978

[22] Filed: Dec. 15, 1976

[30] Foreign Application Priority Data

Dec. 15, 1976 [JP] Japan .................................. 51-148406

[51] Int. Cl.$^2$ ............................................. C08L 51/00
[52] U.S. Cl. ........................................ 260/875; 32/15; 106/35; 260/901; 260/998.11
[58] Field of Search ..................... 106/35; 260/998.11, 260/885, 875, 901; 32/15, 12

[56] References Cited

U.S. PATENT DOCUMENTS

| 3,751,399 | 8/1973 | Lee, Jr. et al. ............................ 32/15 |
| 3,923,740 | 12/1975 | Schmitt et al. .................. 260/998.11 |

*Primary Examiner*—Lorenzo B. Hayes
*Assistant Examiner*—Amelia B. Yarbrough
*Attorney, Agent, or Firm*—Oblon, Fisher, Spivak, McClelland & Maier

[57] ABSTRACT

Resinous materials for restoring crowns is disclosed herein, said materials prepared by mixing a modified polymethyl methacrylate in the liquid state with powders of a methacrylic resin polymer.

6 Claims, No Drawings

RESINOUS MATERIALS FOR RESTORING CROWNS

DETAILED EXPLANATION OF THE INVENTION

The present invention relates to a slurried material obtained by mixing powders of methacrylic resin polymer component B with a component A liquefied at normal temperatures by modifying, to a given extent, 2,2-bis(4-methacryloxyethoxyphenyl) propane (hereinafter referred to as "Bis-MEPP") expressed by the following formula:

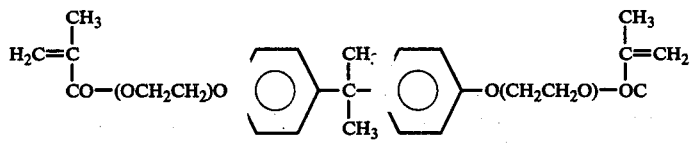

More particularly the present invention provides resinous materials for restoring crowns from which a crown form is fabricated by the build-up technique available to dentistry.

Bis-MEPP that is conceded in dentistry to have excellent physical properties and used widely as the resin monomer for crowns exhibits a crystalline state at normal temperatures. Thus, this Bis-MEPP is disadvantageous in that it must be first liquefied by a heating step employing a complicated apparatus and involving considerably troublesome manipulations, when it is used as the resin for fabricating crowns by the piling up technique.

With a view to eliminating the above-mentioned drawback, the present invention allows Bis-MEPP being a crystalline product at normal temperatures to be liquefied by properly increasing a molar number of ethylene oxide in the molecule of Bis-MEPP, that is, an average addition molar number, (m + n), in the following formula:

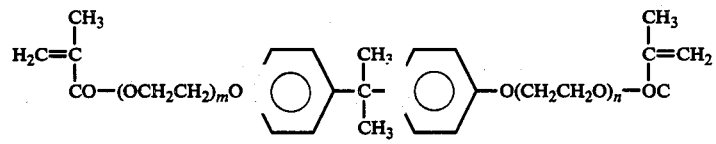

This liquid monomer, 2,2-bis[(4-methacryloxypolyethoxy)phenyl]propane, (hereinafter referred to as "Bis-MPEPP") is then mixed with powders of methacrylic resin polymers to form a slurried product which is found to have a substantially improved workability and provide excellent physical properties to the end product and, therefore, to be well suited for the resinous materials for restoring crowns.

As well known, ceramic and resinous materials are used as the crown facing material for the fabrication of a crown form in which a translucent material is piled upon a metal frame.

The ceramic material has the merits that it is;
(A) great in wear resistance;
(B) not subjected to changes in color;
(C) great in hardness; and
(D) harmless to gingival portion in the mouth.

On the other hand, however, it has the following drawbacks that;

(i) A backing metal (mainly, gold alloy) for the metal frame is required which has a chemical bonding force with respect to the ceramic material;
(ii) Due to its higher sintering shrinkage, ranging from 20 to 30%, and irregular reflection of the ceramic particles, the original shape and color tint are not revealed unless sintered under vacuum.
(iii) Differences from person to person are likely to occur depending upon the manipulation, and a highly advanced technique is required so as to obtain an end product with a desired shape and tint.
(iv) Due to expensive material and sintering furnace, costs are high.
(v) Due to its hardness and brittleness, it may fracture frequently.

In contrast with such a ceramic material, the resin for crown has the following merits, and hence, is enjoying considerable popularity:
(A) The piling operation is easy;
(B) Certain forms and tints are favorably reproduced;
(C) It is cheaper than the ceramic material;
(D) No limitation is given to the metal used; and
(E) Not easily fractured.

In general, the materials for crown resin for use in the piling technique are composed mainly of two components, i.e., powdery and liquid components. Of these, the powdery component includes fine powders of homopolymer of methyl methacrylate (polymethyl methacrylate, hereinafter referred to as "PMMA") or cross-linked methyl methacrylate polymer or these fine powders to which inorganic fillers may be added.

On the other hand, the liquid component includes a polyfunctional monomer with a high boiling point, for instance, ethylene glycol dimethacrylate, triethylene glycol dimethacrylate, trimethylolethane trimethacrylate, neopentyl glycol dimethacrylate, 2,2 — bis — (4 — methacryloxy — 2 — hydroxyphenyl) propane, 2,2 — bis — (4 — methacryloxypropyloxyphenyl) propane, N, N — bis — (hydroxyethyl) — 3,5 — xylidine, diallylphthalates, triallylcyanurates or the like.

The pre-investing resin crown fabricated from these polymers and monomers by piling technique is superior in hardness and wear resistance to the crown and bridge fabricated from the conventional methyl methacrylate monomer and polymer. It is pointed out, however, that due to its relatively larger water-absorbing property, the crown is swelled in the mouth of the patient, separated from the metal frame while in use or subjected to change in color.

Bisphenol A dimethacrylate, 2,2-bis(4-methacryloxyphenyl)-propane, (hereinafter referred to as "BPDMA") and Bis-MEPP have been recently used as the monomers to overcome the above-mentioned drawbacks. These monomers both are present in the crystalline state of normal temperatures and BPDMA has a high melting point ranging from 70 to 80° C. When BPDMA is used as the only monomer component, the resultant polymer is so excessively brittle that the crown and bridge fabricated therefrom may fracture possibly during use. Thus, the independent use of BPDMA is impossible.

Bis-MEPP having a melting point of about 40° C. is advantageous in that, even when used as the only monomer component, the resultant polymer is free from brittleness and thus possess an excellent hardness and wear resistance. It is, therefore, widely accepted as the resin monomer for crowns. Since this monomer exists in the crystalline state at normal temperatures, however, a particular heating apparatus and a special manipulating manner are required so as to fabricate a crown form from a mixture of this monomer and PMMA piled upon the metal frame by a conventional manner available to dentistry. In other words, this crystalline monomer is melted on a heating plate of certain temperatures to form a slurry by adding PMMA-base powders thereto. The resultant slurry is then piled upon the metal frame followed by the pre-polymerization by blowing hot blast of about 90° C. thereto. The polymerization of the thus obtained prepolymer is finally conducted in an electric furnace or a resin-polymerizing bath.

The method for fabricating crowns and bridge making use of this crystalline monomer has the following drawbacks;

(i) For the preparation of an uniform slurry from a mixture of the crystalline monomer and PMMA powders, a particular apparatus is required, which effects the complete melting of this monomer at a given temperature, for instance, about 40° C.

(ii) When a temperature of the heating plate drops or the piling operation is not performed smoothly, this piling operation may be not continued satisfactorily due to the precipitation of the crystalline monomer from the powder/liquid mixture.

(iii) When a temperature of the heating plate rises too high, or the powder/liquid blend is left alone on the plate for an extended period of time, the blend exhibits a paste-like state to lose its fluidity and cure, rendering the piling operation difficult.

(iv) Since the crystalline monomer has a poor compatibility with respect to the PMMA powders and thus air bubbles are easily entrapped therein, the polymerized crown exhibits unfavorable physical properties of strength, hardness or the like, frequently causing changes in color.

The characteristic feature of the present invention lies in the provision of the resinous material for crowns which take full advantage of the excellent physical properties inherent in the Bis-MEPP and moreover, are completely free from the aforementioned drawbacks by using the modified component of Bis-MEPP. Namely, according to the present invention, it has been found that the resinous materials for crowns and bridge having improved physical properties and workability, etc. can be realized by using a slurried material in which methyl methacrylic powders are mixed with Bis-MPEPP liquefied at normal temperatures by properly increasing an average addition molar number of ethylene oxide in the molecule of Bis-MEPP.

Bis-MEPP now available in general to dentistry has the following structural formula (I):

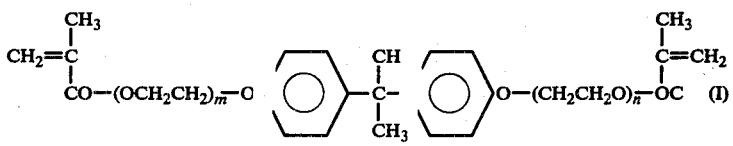

wherein $m = n = 1$, and provides a crystalline monomer at normal temperatures. As the sum of $(m + n)$ representing an average molar number in this formula increases, a melting point of this substance drops. When $(m + n) = 2.2$, this substance affords a condensed liquid of fluidity. Its solidifying point decreases with an increase in the sum of $(m + n)$. When $(m + n)$ is over 2.6, this substance keeps a liquid state even in the refrigerator (less than $-6°$ C.). However, as $(m + n)$ excedes 6, the regularity of the long chain molecular configuration is greatly influenced to again increase a solidifying point, resulting in solidification of this substance.

According to the present invention, the monomer satisfying the relation of $2.2 \leq (m + n) \leq 6$ in the aforementioned formula (I) are used as the monomer component. The monomer in this range affords a liquid monomer with a suitable viscosity ranging from 2,000 to 13,000 cps at normal temperatures. A slurry prepared by mixing this monomer with methyl methacrylic polymer can be subjected to the piling operation without the necessity of a particular heating apparatus. Further, this slurry has the following merits: it is not leached away and it does not exhibit a paste-like state, nor does it cure during operation. In addition, since this monomer shows a favorable affinity with respect to PMMA powders, air bubbles are not substantially entrapped therein during mixing. Incidentally, this liquid monomer is pre-polymerized with PMMA powders faster than the crystalline monomer and thus can be manipulated with a great efficiency. A test relating to the self stability of a slurry prepared by mixing Bis-MPEPP with PMMA powders was conducted using the slurry to which 50 ppm of hydroquinone or butylated hydroxy-P-toluene (BHT) was added. Two years after left alone at room temperatures, the slurry was not subjected to gelation.

A monomer wherein $(m + n)$ is less than 2.2, exhibits a condensed or crystalline state at normal temperatues and thus must be melted and further fluidized by means of a particular apparatus (heating plate) so as to conduct the mixing and piling operations. Further, since air bubbles are readily entrapped during the piling operation, this monomer is not suited for practical use. A monomer wherein $(m + n)$ exceeds 6 moles has a compressive strength (according to the anti-deformation test JIS-T6508) of below 4.5g, a hardness (according to JIS-T6508) of below 16 (k.H.N.) and a water absorption (according to JIS-T6508) of over 0.7 mg/cm².

Thus, this monomer does not meet Japanese Industrial Standards, and is not put into practical use. Accordingly, $(m + n)$ is confined to the following limits, $2.2 \leq (m + n) \leq 6$.

When a mixing ratio of Bis-MPEPP to powders of methacrylic resin polymer is less than 1:3, the resultant slurry has a fluidity increase, rendering the piling operation difficult and hence its practical use impossible. Therefore, the mixing ratio of Bis-MPEPP to PMMA may preferably fall in the range of 1:3 to 4:1.

Several examples of the present invention are illustrated below. PMMA-base polymers having a particle size of 200 to 400 mesh were used as the powdery component. Bis-MPEPP and PMMA powders were mixed together in the mixing ratio of 1:1 to form a slurried mixture of the powders and liquid. The resultant slurry was then piled by a brush according to a conventional method available to dentistry in such a manner that its thickness is in the order of about 0.2 mm, and thereafter, subjected to prepolymerization by blowing hot blast of about 90° C. thereto for about one minute. The foregoing operation was repeated to form a product of uniform thickness and desired shape, which was finally polymerized by heating the same at 140° C. for 10 minutes. The results are shown in Table 1. As evident from the table, the workability and physical properties are remarkably improved in comparison with those of the samples prepared from a conventional crystalline monomer.

Although the following examples show some embodiments of the present invention, it is understood that the scope of the present invention are not limited thereto.

EXAMPLE I

Slurry prepared by mixing Bis-MPEPP of (m + n) = 2.2 moles (average) in the formula (I) with PMMA-base powders (containing 0.3 wt.% of benzoyl peroxide).

EXAMPLE II

Slurry prepared by mixing Bis-MPEPP of (m + n) = 2.6 moles (average) in the formula I (containing 50 ppm of BHT) with methyl methacrylate powders cross-linked by Bis-MPEPP (containing 0.3 wt.% of 2,5-dimethyl-2,5-dihydroperoxyhexane 3).

EXAMPLE III

Slurry of Example I using Bis-MPEPP of (m + n) = 4 moles (average).

EXAMPLE IV

Slurry comprising a mixture prepared by blending Bis-MPEPP of (m + n) = 6 moles with BPDMA in the mixing ratio (wt.) of 7:3 which is used as the liquid component, and the same powder component as in Example I.

EXAMPLE V

Slurry comprising a mixture prepared by mixing Bis-MPEPP (m + n) = 6 moles and (m + n) = 2 moles in the mixing ratio (wt.) of 1:1, and the same powder component as in Example I.

EXAMPLE VI (Control)

Slurry comprising conventional Bis-MEPP crystalline monomer (containing 50 ppm of BHT) which is used as the liquid component, and the same powder component of Example I.

The polymerization was conducted by first melting crystalline monomer on the heating plate in a conventional manner, and adding powders of the same weight ratio to form a slurried mixture of the powder and liquid, followed by the polymerization according to the manner of Examples I to V.

TABLE

| | Hardness (K.H.N.) JIS - T 6508 | Water absorption (mg/cm$^2$) JIS - T 6508 | Anti-deflection strength (Kg) JIS - T 6508 | Pre-curing time (sec) thickness 0.2mm heating temperature 80° C | heating operation during blending |
|---|---|---|---|---|---|
| Example (I) | 21.3 | 0.40 | 8.5 | 50 | None |
| (II) | 22.1 | 0.41 | 8.5 | 45 | None |
| (III) | 20.1 | 0.48 | 9.0 | 40 | None |
| (IV) | 20.3 | 0.45 | 8.5 | 50 | None |
| (V) | 20.0 | 0.49 | 8.0 | 55 | None |
| Control (conventional material) | 19.2 | 0.63 | 5.5 | 150 | Yes |

What is claimed as new and intended to be secured by Letters Patent of the United States is:

1. A slurried resinous material for restoring crowns, comprising:
a liquid component A having the following formula:

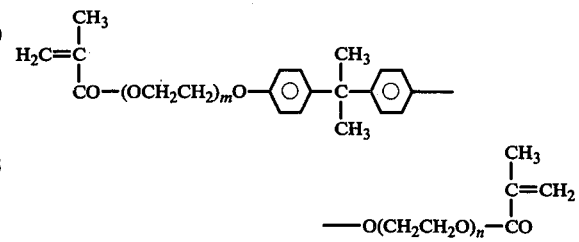

wherein the average molar amount of ethylene oxide units ( m + n), present satisfies the relation: $2.2 \leq (m + n) \leq 6$, and a power component B which is a methacrylic resin polymer,
wherein said liquid component A is mixed with said powder component B in proportions ranging from 1:3 to 4:1.

2. The slurried material of claim 1, wherein said methacrylic resin polymer is polymethylmethacrylate or cross-linked polymethylmethacrylate.

3. A method for restoring dental crowns, comprising:
forming a slurry mixture by mixing a liquid component A having the formula:

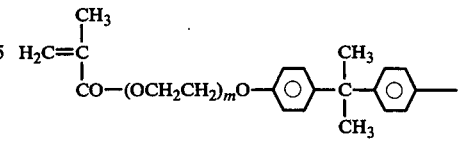

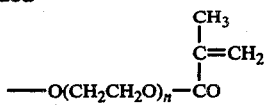

wherein the average molar amount of ethylene oxide units (m + n), present satisfies the relation: $2.2 \leq (m + n) \leq 6$, and a powder component B which is a methacrylic resin polymer, wherein said liquid component A is mixed with said powder component B in proportions ranging from 1:3 to 4:1, applying said slurry mixture to a crown substrate; and polymerizing the mixture applied to said crown substrate.

4. The method of claim 3, wherein said piled mixture is prepolymerized by subjecting said piled mixture to a blast of hot air of about one minute, and then completing polymerization by heating said prepolymerized mixture to about 140° C.

5. The slurried material of claim 1, wherein said liquid component A is mixed with a compound of said formula having values of (m + n) of 2.6 to about 4.

6. The slurried material of claim 5, wherein the viscosity of said liquid component A is controlled by admixture with 2,2-bis(4-methacryloxyphenyl)propane.

UNITED STATES PATENT AND TRADEMARK OFFICE
CERTIFICATE OF CORRECTION

PATENT NO. : 4,134,930
DATED : January 16, 1979
INVENTOR(S) : Takao Kubota

It is certified that error appears in the above-identified patent and that said Letters Patent are hereby corrected as shown below:

Please Correct the Priority Information to read as follows:

[30] Dec. 15, 1975 [JP] Japan.............50-148406

Signed and Sealed this

Twenty-second Day of May 1979

[SEAL]

Attest:

RUTH C. MASON
Attesting Officer

DONALD W. BANNER
Commissioner of Patents and Trademarks